United States Patent [19]
Volk

[11] Patent Number: 5,424,789
[45] Date of Patent: Jun. 13, 1995

[54] OPTICAL DEVICE FOR USE WITH A SLIT LAMP BIOMICROSCOPE

[76] Inventor: Donald A. Volk, 9378 Jackson, Mentor, Ohio 44060

[21] Appl. No.: 68,894

[22] Filed: May 28, 1993

Related U.S. Application Data

[63] Continuation of Ser. No. 604,547, Oct. 29, 1990, Pat. No. 5,216,456.

[51] Int. Cl.$^6$ .............................................. A61B 3/10
[52] U.S. Cl. .................................... 351/216; 351/205; 351/217
[58] Field of Search ............... 351/214, 216, 221, 206, 351/217, 218, 219

[56] References Cited

U.S. PATENT DOCUMENTS

| | | | |
|---|---|---|---|
| 2,622,473 | 12/1952 | Littmann | 351/216 |
| 3,944,343 | 3/1976 | Mueller, Jr. | 351/214 |
| 4,478,499 | 10/1984 | Hoerenz | 351/221 |
| 4,874,236 | 10/1989 | Abraham | 351/214 |
| 5,216,456 | 6/1993 | Volk | 351/216 |

Primary Examiner—William L. Sikes
Assistant Examiner—Hung Xuan Dang
Attorney, Agent, or Firm—Oldham Oldham & Wilson & Co.

[57] ABSTRACT

An optical device comprising a lens and an adjustable lens holder which is adapted to be positioned on an existing slit lamp biomicroscope such that the lens may be selectively positioned in the path of the illuminating light beam from the slit lamp light source. In one embodiment of the invention, the adjustable holder is designed to be rotatably positioned in association with the slit lamp light illumination apparatus and in relation to the projecting or objective lens of the slit lamp illumination system. The lens holder is designed to pass a narrowed zone on support structures associated with the light illumination apparatus and to frictionally engage a portion of the support structure while allowing rotation of the lens into and out of the path of the illuminating light beam. Alternatively, as the design of the slit lamp biomicroscope varies, the lens holder may vary so as to allow frictional engagement with a portion of the illuminating light source structure, wherein the lens will be pivotable into and out of the path of the illuminating light beam adjacent the projecting lens of the slit lamp light source. The lens of the optical device can be made of glass or plastic, and the lens holder may be constructed so as to allow various lenses to be quickly and easily removed and replaced by another lens. Alternatively, the lens holder may be provided with a plurality of lenses which may be selectively positioned in the path of the illuminating light beam. Additionally, a plurality of the optical devices may be used with the same slit lamp biomicroscope to modify the optical characteristics of the light source selectively and efficiently. Modification may include filtering of the illuminating light or adding divergence of convergence to the light rays to achieve various desired optical characteristics.

16 Claims, 3 Drawing Sheets

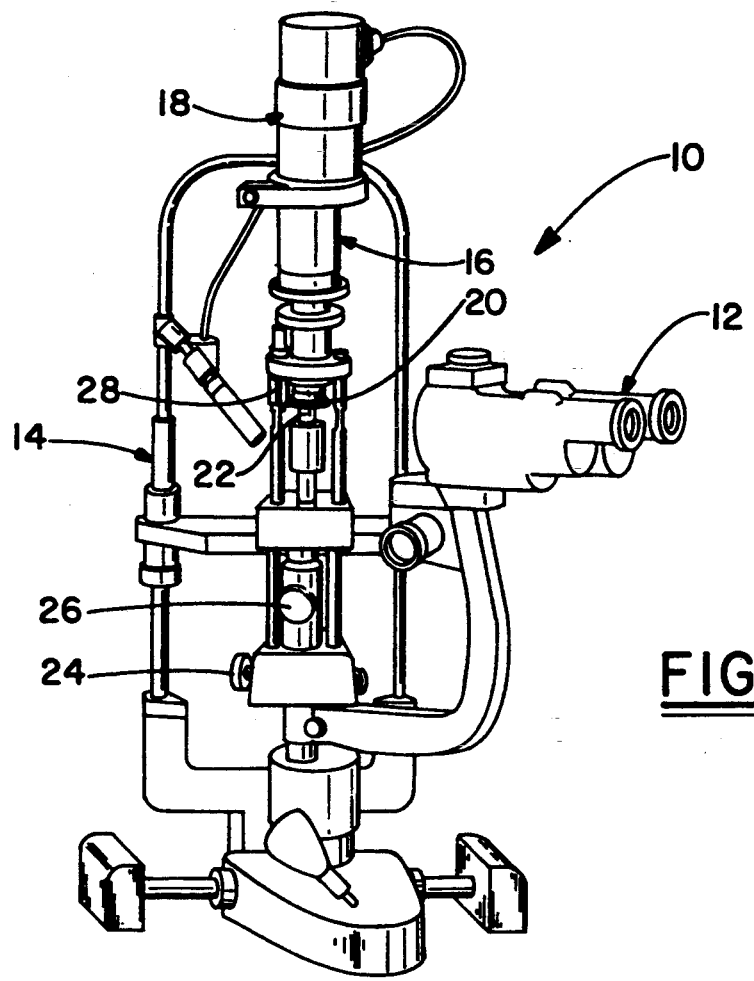
FIG.-1
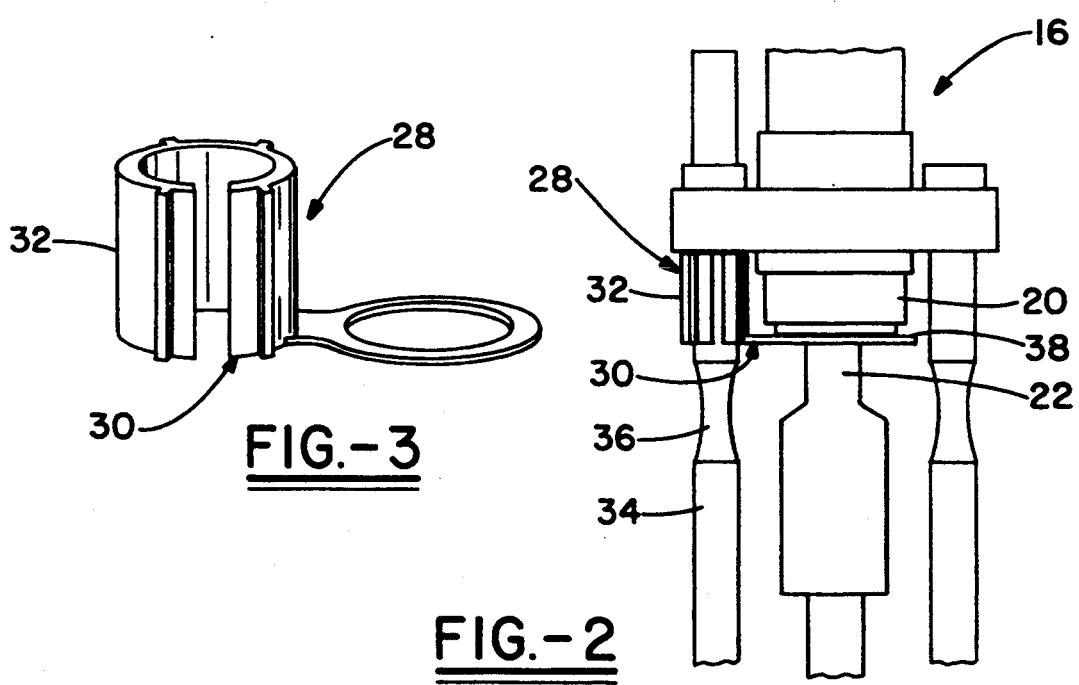
FIG.-3
FIG.-2

OPTICAL DEVICE FOR USE WITH A SLIT LAMP BIOMICROSCOPE

This is a continuation of application Ser. No. 07/604,547, filed on Oct. 29, 1990, now a U.S. Pat. No. 5,216,456.

BACKGROUND OF THE INVENTION

The present invention is directed an optical device which is utilized in conjunction with a slit lamp biomicroscope, when the biomicroscope is used for indirect ophthalmoscopy or other examination procedures, so as to obtain desired optical characteristics by modifying the illuminating light beam emitted from the projecting lens of the slit lamp biomicroscope. More particularly, the invention is directed to an optical device which may be simply positioned and retained on a conventional state-of-the-art slit lamp biomicroscope in association with the projecting lens thereof to modify the illuminating light beam by filtering, enlarging or otherwise modifying the beam.

The slit lamp biomicroscope has long been utilized as a tool for ophthalmic examinations such as indirect ophthalmoscopy, gonioscopy, fundoscopy or the like. Various forms of slit lamp biomicroscopes have been developed such as the Haag-Streit slit lamps or the Zeiss slit lamps, which essentially achieve similar desired characteristics in the biomicroscope, but have been designed somewhat differently. Conventionally, the slit lamp biomicroscope includes a microscope head, an illumination system producing a slit beam which may be rotated or tilted by the user, as well as patient support structure to facilitate a proper and comfortable examination. In particular, the illumination system of the slit lamp biomicroscope varies with manufacturing designs, but in most cases will allow the slit light beam to be rotated 90° from vertical and may also allow the light path to be inclinable by an angle ranging between 0° and 20°. The entire illumination assembly may be tilted to provide these characteristics or tilting may be accomplished by a rotatory prism or tilting mirror structure. The beam size is also adjustable from an extremely narrow slit to several millimeters in width, and the height of the slit may be controlled by a variable size aperture or diaphragm structure.

Using a slit lamp biomicroscope, observation of particular aspects of the examined eye may be enhanced by only transmitting particular portions of the light spectrum found in the illuminating light beam from the slit lamp light source. Various state-of-the-art slit lamp biomicroscopes have recently included built-in color filters to allow enhanced observation of different aspects of the examined eye. For example, a red filter may be utilized so as to better enable observation of blood vessels on the fundus of the eye. Although various filters have been built in slit lamp biomicroscopes, other desirable characteristics have not been built in to the biomicroscopes and therefore are not available for use during various examination techniques. Similarly, many slit lamp biomicroscopes are not provided with any filtering apparatus at all, or may only include several of the possible desired filters.

Under many circumstances, an indirect ophthalmoscopy lens device is used for examination of a patient, wherein the illuminating light beam from the slit lamp biomicroscope light source is directed through the indirect ophthalmoscopy lens which is held adjacent to the patient's eye. In use with an indirect ophthalmoscopy lens, the maximum possible size of the illuminating light beam reaching the indirect ophthalmoscopy lens is no more than 12 mm in diameter for state-of-the-art biomicroscopes. The indirect ophthalmoscopy lens itself may be of relatively large diameter, and it would be desirable to enable eliminating light beam from the slit lamp light source to fully illuminate the indirect ophthalmoscopy lens for full illumination of the examined eye.

SUMMARY OF THE INVENTION

Based upon the foregoing, there is found to be a need for an optical device which may be simply added or retrofit to the slit lamp biomicroscope to modify the size, color, polarization or other aspects of the illuminating light beam from the slit lamp light source and used for illumination in various examination techniques. It is therefore a main object of the invention to provide an optical device which is added or retrofit to the state-of-the-art slit lamp biomicroscope to enable selective modification of the illuminating light beam from the biomicroscope.

Another object of the invention is to provide an optical device for use with an existing slit lamp biomicroscope which will allow modification of the illuminating light beam from the slit lamp light source in a selective and variable manner, and may include filtering means, polarizing means or other means by which the optical characteristics of the illuminating light beam are modified.

It is another object of the invention to provide an optical device for use with an existing slit lamp biomicroscope to enable repositioning of the image of the filament of the slit lamp light source so as to facilitate examination procedures such as indirect ophthalmoscopy.

It is another object of the invention to provide an optical device which will enable the size of the illuminating light beam from the slit lamp light source to be increased in size to facilitate various examination procedures.

These and other objects of the invention are achieved by an optical device comprising a lens and an adjustable lens holder which is adapted to be positioned on an existing slit lamp biomicroscope such that the lens may be selectively positioned in the path of the illuminating light beam from the slit lamp light source. In one embodiment of the invention, the adjustable holder is designed to be rotatably positioned in association with the slit lamp light illumination apparatus and in relation to the projecting or objective lens of the slit lamp illumination system. The lens holder is designed to pass a narrowed zone on support structures associated with the light illumination apparatus and to frictionally engage a portion of the support structure while allowing rotation of the lens into and out of the path of the illuminating light beam. Alternatively, as the design of the slit lamp biomicroscope varies, the lens holder may vary so as to allow frictional engagement with a portion of the illuminating light source structure, wherein the lens will be pivotable into and out of the path of the illuminating light beam adjacent the projecting lens of the slit lamp light source. The lens of the optical device can be made of glass or plastic, and the lens holder may be constructed so as to allow various lenses to be quickly and easily removed and replaced by another lens. Alternatively, the lens holder may be provided with a plurality of lenses which may be selectively positioned in the path of the illuminating light beam. Additionally, a plurality of the optical devices may be used with the same slit lamp biomicroscope to modify the optical characteristics of the light source selectively and efficiently.

BRIEF DESCRIPTION OF THE DRAWINGS

These and other objects and advantages of the optical device will become apparent upon a further reading of the detailed description in conjunction with the drawings wherein:

FIG. 1 shows a conventional state-of-the-art slit lamp biomicroscope with the optical device of the invention operatively positioned thereon;

FIG. 2 as an enlarged cut away view of the slit lamp biomicroscope as seen in FIG. 1, showing positioning of the optical device thereon;

FIG. 3 is an enlarged perspective view of a first embodiment of the optical device for use with the slit lamp biomicroscope as seen in FIG. 1;

DETAILED DESCRIPTION OF THE INVENTION

Figure 4:
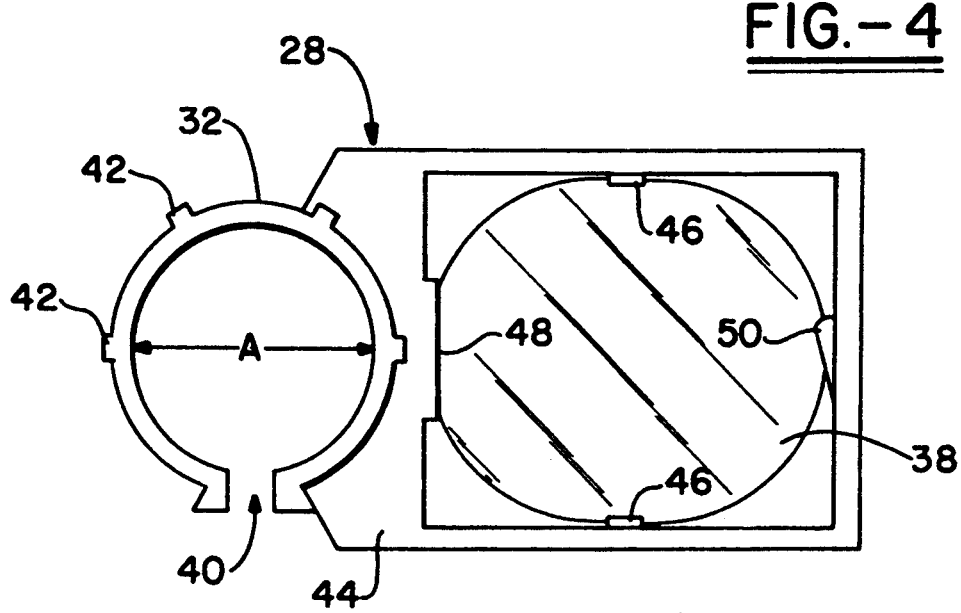
FIG. 4 is an enlarged top view of the optical device as seen in FIG. 3.

Referring now to FIG. 1, there is shown a conventional state-of-the-art slit lamp biomicroscope 10, manufactured by Haag-Streit, which is available in the market. The biomicroscope 10 is designed for observation of the eye, and includes various structure to facilitate such observation. The microscope head 12 includes eye pieces which can be corrected to the accommodating error of the physician and is usable to magnify a produced image by 5 to 45 times, as an example. A patient support structure 14 includes a chin and forehead rest for the comfort of the patient as well as to maintain position of the examined eye during examination. The illumination system 16 generally includes an illuminating light source 18, and a lens system with one or more lenses (not shown) disposed in the path of the light beam originating from a small filament within the biomicroscope. The lens system acts to refract the light beam to create a diverging bundle of light rays. The diverging bundle of light rays is directed through a projecting or objective lens 20, forming an exit opening of the illumination systems to a reflecting mirror 22 so as to be directed toward the eye or an indirect ophthalmoscopy lens utilized for examination of a patient. The illumination system 16 includes a slit beam adjustment 24 as well as adjustment for centering or decentering the slit image at 26. In such adjustments, the position of the projecting lens 20 is not modified, but the position of the reflecting mirror 22 may be. The entire illumination system as well as microscope system may be raised or lowered for proper examination of a particular patient. The optical device of the invention is shown at 28 and provides a lens within a lens holder which is positioned between the projecting lens 20 and reflecting mirror 22 of the slit lamp biomicroscope 10. In the biomicroscope 10 as shown in FIG. 1, the lens holder may be positioned on supporting structure of the illumination system so as to be selectively positioned in the path of the illuminating light beam regardless of the adjustments made with respect to the slit image.

Turning now to FIG. 2, the positioning and operation of a first embodiment of the optical device of the invention will become more apparent. The area of the projecting lens 20 of the illumination system 16 of the biomicroscope is shown enlarged with the optical device 28 thereon. The optical device 28 includes a lens holder 30 with a first body portion 32 which is adapted to engage a supporting bar 34 associated with the illumination system 16. The supporting bar 34 includes a narrowed portion 36 which allows for binocular vision using the microscope portion of the biomicroscope without interference from these supporting bars. The first body portion 32 of the device 28 therefore includes a semi-circular body with a longitudinal gap allowing the body portion 32 to be slipped over the narrowed portion 36 of the supporting bar 34. The lens holder 30 may be constructed of a resilient material such as plastic such that the longitudinal gap in the body portion 32 may be spread apart slightly to fit around narrowed portion 36 of the supporting bar 34. The inside diameter of the semi-circular body portion 32 then corresponds to the diameter of the supporting bar 34 so as to frictionally engage the bar 34 at locations of normal diameter adjacent to narrowed portion 36. It should be evident that in this manner, the optical device 28 may be slipped on to the supporting bar 34 to an operative position relative to the projecting lens 20 and reflecting mirror 22 by properly positioning the lens portion 38 at the gap between projecting lens 20 and reflecting mirror 22 and rotating lens holder 30 to the position as seen in FIG. 2. Thus, selective use of the optical device 28 is accomplished very easily and effectively when modification of the optical characteristics of the illuminating light beam are desired.

Figure 5:
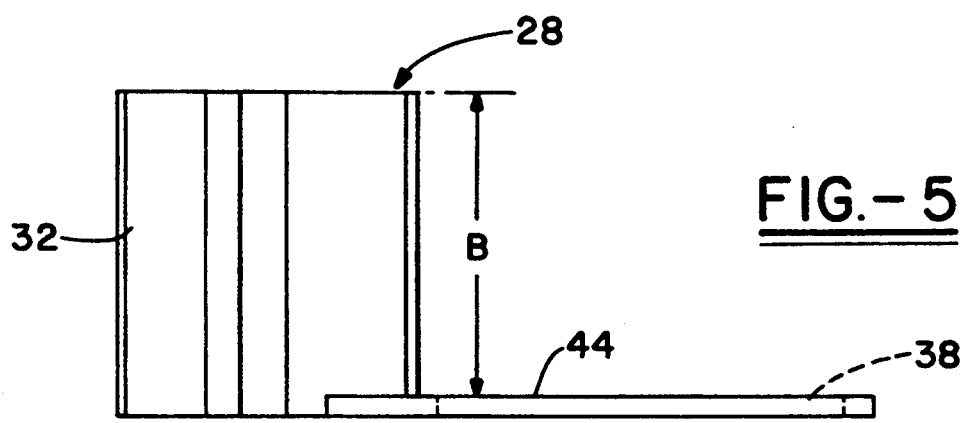
FIG. 5 is an enlarged side elevation of the optical device as seen in FIG. 3.

The optical device of this embodiment is seen in more detail in FIGS. 3-5, wherein the lens holder 30 includes the first body portion 32 being of semi-circular configuration and having a gap 40 formed therein having dimensions to allow the body portion 32 to slip over the support structure of the illuminating system of a biomicroscope as previously described. The inner diameter of the semi-circular portion of body member 32 as shown by A in FIG. 4 is of slightly smaller diameter than the supporting structure of the illumination system such that the semi-circular portion will frictional engagement with the support structure and yet allow longitudinal and rotational movement of the body portion thereon. The body portion 32 may also include outwardly extending projections 42 to more easily allow the user to rotate body member 32 on the support structure of the biomicroscope.

The optical device 28 may further comprise a lens holding portion 44 extending from the semi-circular portion 32 in adapted to engage and secure a lens 38 therein. The lens holding portion 44 may be adapted to engage and secure the lens 38 by means of suitable structure such as tabs 46 and 48 creating a suitable slot in the lens holding portion 44 for positioning lens 38. It also may desirable to provide a means by which the lens 38 can be removed and replaced with another type of lens to allow the optical device 28 to be adapted for a variety of uses. A suitable means may be a pivotable flange 50 extending from one edge of the opening in lens holding portion 44, which may be pivoted into a lens engaging position for retention of lens 38 in the portion 44, or pivoted to a non-lens engaging position for removal of lens 38. Other suitable means may be provided for allowing the lens 38 to be removed and replaced selectively by the user.

The dimensions of the lens holding portion 44 are such that the lens 38 extends entirely over the projecting lens 20 of the slit lamp biomicroscope as seen in FIGS. 1 and 2 and allows for adjustment of the slit beam without degrading the modification of optical characteristics accomplished by lens 38. The optical device 28 as seen in these figures is shown as having a rectangular lens portion 38, but any desired shape may be utilized as for example a generally circular shape or having convex or concave surfaces thereon.

In the invention, modification of the illuminating beam generated by the biomicroscope may include filtering of the illuminating light by any of a variety of filters such as colored filters or polarizing filters. In the case of color filters, the lens 38 may be constructed of a homogeneous transparent plastic material or a homogeneous transparent glass material in which the spectral transmission characteristics of the transparent optical material is high. The filtering lenses may comprise an orange-red colored optical material which will limit the spectral transmission of the illuminating light to the yellow-orange-red portion of the visible spectrum, so as to cut out green portions of the illuminating light to better enable observation of blood vessels in the eye. Alternatively, a green colored optical material may limit the spectral transmission to the green portion of the visible spectrum to eliminate red portions thereof and to enable observation of the nerve fiber layer in the eye. A yellow colored optical material will enable spectral transmission of the green-yellow-orange-red portion of the visible spectrum which will eliminate blue and violet portions thereof to provide patient safety and comfort. The optical material may comprise a dichroic filter glass or the like. As still another example, the optical material may be transparent to the visible spectrum, but may act to filter portions of the non-visible spectrum which may be present in the illuminating light.

In another desirable embodiment, the lens 38 may be a polarizing lens, wherein the light from the slit lamp light source is refracted through the lens to be polarized in a specific direction. If a polarizing filter, with its direction of polarization at 90° to the direction of polarization of the incident light beam, is placed in front of both objective lenses of the biomicroscope, the unwanted specular or glare reflection from an indirect ophthalmoscopy lens and cornea, which remains polarized in the same direction as the incident light beam, will not be transmitted through the polaroid filter. In this way, the aerial image of the fundus as produced by the indirect ophthalmoscopy lens will be seen clearly and without overlying annoying glare spots. The use of a polarizing filter to remove glare is especially useful when photographing the aerial image of the fundus utilizing the slit lamp biomicroscope in conjunction with an attached camera. The lens 38 may be a single element of glass or plastic or may be a composite lens consisting of a clear white portion combined with a colored filter or polarizing filter or both.

In another desired embodiment, the lens used in association with the optical device may be a lens having refractive power, such as a negative power or positive power lens. Such a lens may be desirable in that it has been found that with the maximum slit opening of the biomicroscope, the maximum possible size of the illuminating light beam from the slit lamp light source as the beam reaches an indirect ophthalmoscopy lens or the eye of the patient is no more than 12 mm in diameter. If an indirect ophthalmoscopy lens is utilized for examination, only a part of the indirect ophthalmoscopy lens is illuminated by the incident light beam from the slit lamp light source, and correspondingly, only a similarly sized image of the indirect ophthalmoscopy lens on the fundus of the eye will be formed and only a portion of the fundus will be illuminated directly, although some indirect illumination may be generated from light scattering within the eye. The brightly illuminated portion of the aerial image of the fundus produced by an indirect ophthalmoscopy lens thus will be limited in size and significantly smaller then it would be had the indirect ophthalmoscopy lens been fully illuminated by the incident light beam from the biomicroscope. By utilizing a lens having refractive power in the optical device of the invention, the incident light beam may be increased in size such that the entire extent of an indirect ophthalmoscopy lens will be illuminated. Full illumination of the indirect ophthalmoscopy lens will result in formation of an image of the light source at a point near the center of the pupil of the eye, from which light will diverge to form a broad illuminated area of the fundus the size of the image of the indirect ophthalmoscopy lens on the fundus. Light is diffusely reflected from all illuminated points in the fundus and from each illuminated point a diverging bundle of light rays pass through the pupil of the eye and through the cornea to be incident upon the indirect ophthalmoscopy lens. The indirect ophthalmoscopy lens will then form a real inverted aerial image of the fundus which is viewed through the biomicroscope, and which will have the same level of illumination across its entire extent and will appear, when viewed through the biomicroscope, to fill the entire indirect ophthalmoscopy lens. It should be evident that a lens having refractive power may include a filtering capacity if constructed as a composite lens or may be used in conjunction with a separate filter lens. The characteristics of the optical device having a lens with refractive power will be described in more detail as the description proceeds.

It should be evident from the foregoing that the optical device 28 can be instantly positioned with its lens portion in front of and coaxial with the projecting or condensing lens of the slit lamp biomicroscope and just as simply be displaced from this position. The device makes it very practical for the slit lamp biomicroscope to be used in its usual fashion in examining the eye, and while the patient is still seated in front of the slit lamp, to position the optical device 28 in front of the condensing lens to modify the optical characteristics of the illuminating light so as to perform various other examination techniques as desired. In the preferred embodiment, the optical device 28 is positioned directly adjacent the condensing or projecting lens 20 of the slit lamp light source, although it may be positioned at some other convenient distance from the condensing lens, between the condensing lens and the oblique mirror 22 of the biomicroscope. As seen in FIG. 5, the height of the body portion 32 as indicated at B is such that the body portion may be slid up against other supporting structure of the illumination system so as to automatically position the lens holding portion 44 at the proper location to be rotated into a closely adjacent position relative to condensing lens 20. It should also be evident that another optical device 28 may be used in conjunction with another supporting rod 34 on the opposite side of condensing lens 20, which may similarly be rotated into an out of position in the path of the illuminating light. In such a situation, it may be desirable to provide a spacer in conjunction with the body portion 32 which can be slid onto the supporting bar 34! at its narrowed portion 36 in a similar manner to easily adjust the position of the lens holding portion 44 relative to the condensing lens 20. Such a spacer may simply comprise a semi-circular body portion having a predetermined height and a gap so as to be slid over the narrowed portion 36 of the support bar 34 to be used in conjunction with the optical device 28.

Figure 6:
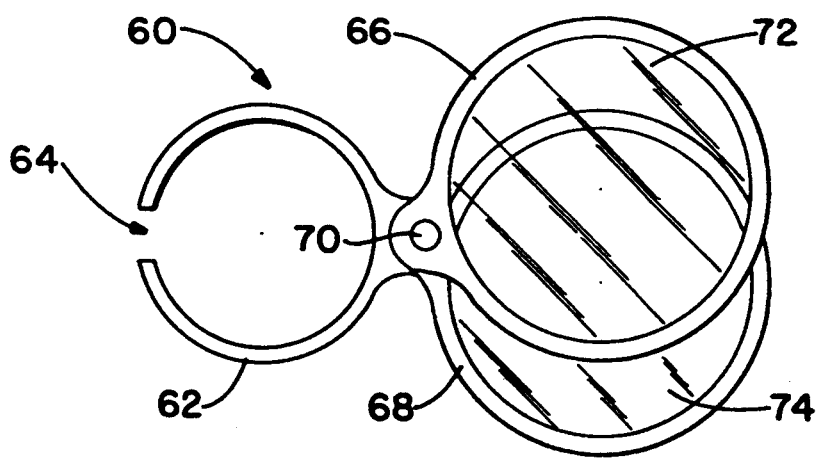
FIG. 6 is an enlarged top elevational view of an alternate embodiment of the optical device of the invention.

Turning now to FIG. 6, an alternate embodiment of the optical device is shown to include a plurality of lenses which may be selectively positioned in the path of the illuminating light as desired by the user. In this embodiment, the optical device 60 again may include a semi-circular body portion 62 having a gap 64 therein which is adapted to slip over a narrowed portion of supporting bars on the illumination system of the biomicroscope in a similar manner to that previously described. The optical device 60 may further comprise a plurality of lens holding portions 66, 68, etc., which are secured to the body portion 62 by means of a pin or the like at 70. The lens holding portions 66 and 68 may therefore rotate or pivot about pin 70 so as to selectively position each of the plurality of lens holding portions into the path of the illuminating light beam separately or in conjunction with one another. Each of the lens holding portions 66, 68, etc. will include a lens portion 72, 74, etc. which may be of the types of lenses previously described to provide the desired modification of the optical characteristics of the illuminating light beam.

Figure 7:
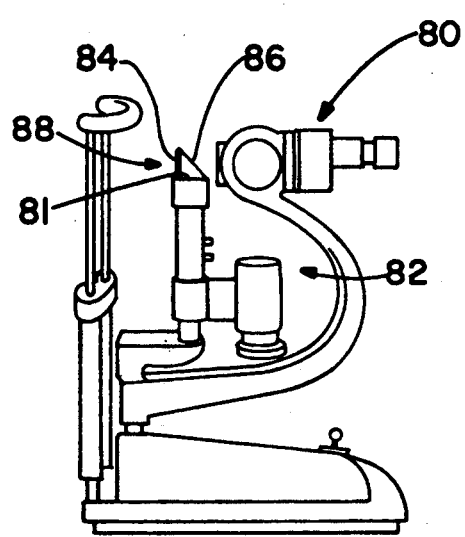
FIG. 7 shows another type of slit lamp biomicroscope with an alternate embodiment of the optical device positioned thereon.

Another type of slit lamp biomicroscope is shown in FIG. 7, which is similar to those manufactured by Zeiss or the Bausch & Lomb Thorpe slit lamp. This type of slit lamp includes many of the same features as described with respect to the biomicroscope of FIG. 1, but does not include the same illumination system as described therein. In the biomicroscope 80, the illumination system 82 comprises a condensing lens 84 forming an exit opening for light rays to emerge from the illumination system 82. The condensing lens 84 is positioned relative to an oblique mirror 86 in association with housing 81. With such a design, the optical device 88 is operatively positioned to allow modification of the illuminating light beam similarly to that previously described. As seen more clearly in FIG. 8, a first embodiment of the optical device 88 includes a lens holding portion 90 which is adapted to be placed into the path of the illuminating light beam passing through the condensing lens 84. The lens holding portion 90 has a lens 92 secured to therein in a manner similar to that previously described to allow easy removal and replacement of the lens 92 by the user for adaptability of the device to various examination procedures. The lens holding portion 90 is pivotally secured to a first body portion 94 which is adapted to be secured to the housing 81 of the condensing lens 84 and oblique mirror 86 of the biomicroscope 80. The first body portion 94 may be secured by means of an adhesive tab 96 or other suitable means to secure it in its operative position on the biomicroscope. A hinge means 98 attaches the first body portion 94 to the lens holding portion 90 such that lens holding portion 90 can pivot about the axis of hinge 98.

In operation, the first body portion 94 is placed on the triangularly shaped housing 81 such that the hinge 98 is positioned at the pinnacle of the housing as seen in FIG. 7. The lens holding portion 90 may then be pivotaly swung into and out of its operative position adjacent and in front of the condensing lens 84 as seen in FIG. 7. To facilitate such movement, a finger tab portion 100 may be provided on lens holding portion 90.

Figure 8:
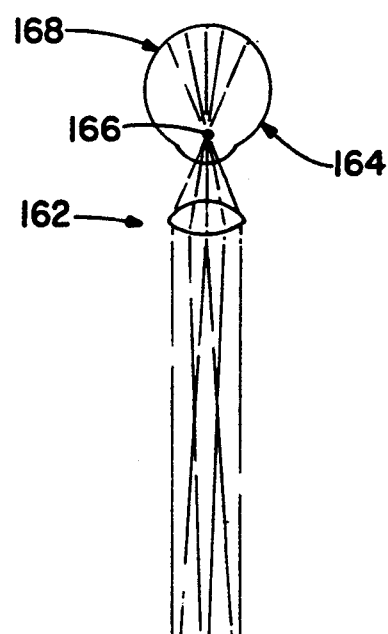
FIG. 8 is an enlarged top elevational view of the optical device for use with a slit lamp biomicroscope as seen in FIG. 7.
Figure 8:
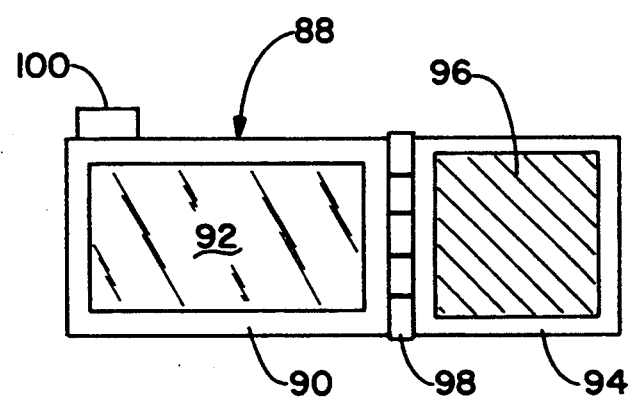
Figure 9:
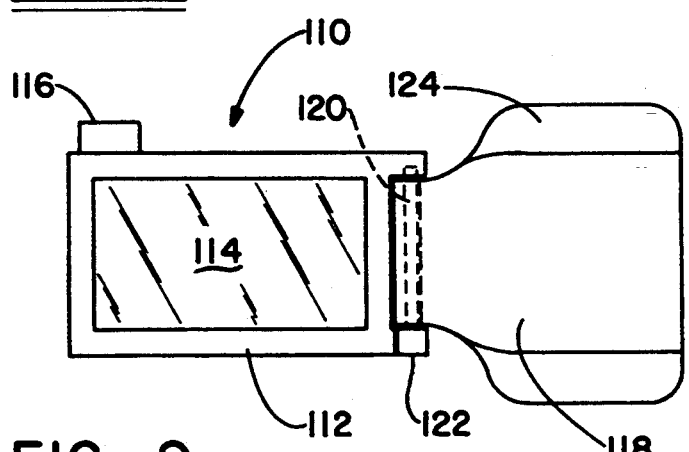
FIG. 9 is an alternate embodiment of the optical device for use with a slit lamp biomicroscope as seen in FIG. 7.

An alternative embodiment of the optical device for use with the biomicroscope as seen in FIG. 7 is shown in FIG. 9 at 110, which again includes a lens holding portion 112 including a lens 114 and finger tab portion 116 similar to that described with reference to FIG. 8. The lens holding portion varies in that it is removably attached to a first body portion 118 to allow replacement of the lens holding portion to provide a variety of lenses for use with the device. The means by which lens holding portion 112 may be attached to first body portion 118 may comprise a post 120 having an enlarged head 122 at the distal end thereof, wherein post 120 may be snap fit into a suitable slot formed in first body portion 118. The post 120 will be rotatable in the slot to allow the pivoting motion of lens holding portion 112 relative to the first body portion 118, so as to pivot the lens 114 into and out of the path of the illuminating light beam in the region adjacent the condensing lens 84. The first body portion may include downwardly extending wing portions 124 which are adapted to slip over the triangularly shaped housing 81. The housing 81 of the biomicroscope will normally have narrowed portions at the location adjacent the microscope head of the biomicroscope to facilitate clear binocular vision without interference from the housing. The first body portion 118 may be constructed of a resilient plastic type material to allow a slight spreading apart of the wing portions 124 for engagement to the housing 81 of the biomicroscope. The wing portions 124 may be easily slipped onto the housing 81 at the location of the narrowed portions, and then slid upwardly so as to be frictionally engaged on the housing in the operative position to allow pivoting of lens holding portion 112 into and out of the illuminating light path. It should be evident that the embodiment of FIG. 9 allows the user to select any desired lens type for use with the body portion 118 which may then be simply positioned on the lens housing of the biomicroscope for operation.

Figure 10:
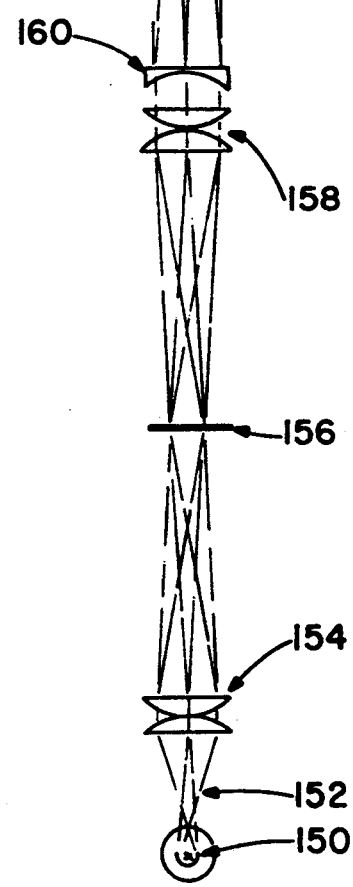
FIG. 10 is a schematic illustration of the illuminating system of a slit lamp biomicroscope including placement of the optical device of the invention in the path of the illuminating light beam from the slit lamp light source, wherein the lens of the device has dioptric power which increases the divergence of the light beam from the slit lamp light source incident upon an indirect ophthalmoscopy lens.

Turning now to FIG. 10, there is shown a schematic illustration of the optics of a slit lamp biomicroscope wherein the optical device of the invention is utilized as a beam enlarger to increase the divergence of the illuminating light beam from the slit lamp light source which will be incident upon an indirect ophthalmoscopy lens as an example. As mentioned previously, when the biomicroscope is used for indirect ophthalmoscopy, the indirect ophthalmoscopy lens will normally have a relatively large diameter lens such as described in U.S. Pat. No. 4,738,521. In state-of-the-art slit lamp biomicroscopes, the maximum size of the illuminating light beam as the beam reaches the indirect ophthalmoscopy lens positioned adjacent the eye under examination, is no more than 12 mm in diameter. Thus, the maximum possible size of the illuminating light beam is less than the diameter of the indirect ophthalmoscopy lens, and it therefore may be desirable to increase the size of the incident light beam upon the indirect ophthalmoscopy lens to the extent that the entire indirect ophthalmoscopy lens is illuminated. By illuminating the indirect ophthalmoscopy lens to its full extent, the aerial image of the fundus will be uniformly illuminated and will correspond to the full extent of the indirect ophthalmoscopy lens.

Additionally, in an emmettopic eye, the aerial image of the fundus produced by an indirect ophthalmoscopy lens as seen of a slit lamp biomicroscope, will be in the anterior focal plane of the indirect ophthalmoscopy lens. With an adequately dilated pupil and the slit aperture fully opened, the produced aerial image will be approximately one centimeter in diameter and will be coplanar with the effective light source and object plane of the biomicroscope. Alternatively, in a myopic eye, the aerial image will be slightly closer to the indirect ophthalmoscopy lens, and conversely with hypermetropia, the image will be slightly farther from the indirect ophthalmoscopy lens. In these situations, the biomicroscope must be moved slightly closer or slightly further away from the indirect ophthalmoscopy lens respectively, in order to allow sharp focusing upon the aerial image produced by the lens. Should the pupil of the examined eye be of relatively small diameter, light from an indirect ophthalmoscopy lens will be blocked from the fundus, which will result in a decrease of brightness and size of the corresponding aerial image produced by the lens. Therefore, it may be desirable to reduce the size of the converged incident light beam from a slit lamp biomicroscope at the center of the entrance pupil of the examined eye so as to permit illumination of the fundus corresponding to the full extent of the pupillary aperture. By reducing the size of the pupillary image of the light source filament at the center of the pupil of the examined eye, indirect ophthalmoscopy performed with the slit lamp biomicroscope on eyes with undilated pupils may be facilitated.

Turning to FIG. 10, an example of the use of the optical device to accomplish the above goals is shown in relation to the optical characteristics of the slit lamp biomicroscope in use for indirect ophthalmoscopy. The slit lamp biomicroscope includes a light source 150 being a small filament within the biomicroscope and producing diverging bundles of light rays 152 which are directed toward lenses 154. The lenses 154 produce a converging bundle of light rays directed toward aperture stop 156 of the biomicroscope. The condensing lens 158 of the biomicroscope will thus receive converging bundles of light rays from the aperture stop 156, and will produce diverging bundles of light rays which are directed toward the examined eye 164. The optical device 160 of the invention is positioned closely adjacent the condensing lens 158 of the biomicroscope as previously described, and in this embodiment is shown as a negative power lens. It is well known that a negative lens adds divergence to a homocentric beam of light incident upon the lens, and thus the divergence of the homocentric bundles of light rays from condensing lens 158 is increased so that the light rays incident upon an indirect ophthalmoscopy lens 162 will fully illuminate the lens 162 as desired. It can be seen in this schematic illustration that the use of the optical device 160 having a negative power lens will result in a repositioning of the effective and virtual light source to a position 166 which is closer to the condensing lens 158. A wider beam of light is thus produced by the lens of the optical device 160 even though the size of the aperture stop 156 remains unchanged. The diameter of the aperture stop 156 may be the maximum diameter, wherein the power of the lens in the optical device 160 is chosen to increase divergence from condensing lens 158 to achieve maximum illumination of the indirect ophthalmoscopy lens 162. Alternatively, the aperture stop 156 may be less then maximum, wherein an increase in power of the lens in the optical device 160 can result in a compensatory widening of the beam of light refracted through the lens of the optical device 160. The adaptability of the optical device to allow the use of various lenses therein may thus allow the slit aperture to be varies while optimizing the widening of the beam.

As an alternative embodiment, the lens of the optical device 160 may be a positive power lens, wherein it is well known that a positive lens will add convergence to an incident homocentric beam of light incident upon the positive lens. The use of a positive power lens may thus result in a repositioning of the effective and real light source of the slit lamp biomicroscope to a position closer to a condensing lens 158, while producing a wider beam of light with the diameter of aperture stop 156 remaining unchanged. Similar to that described with reference to the negative power lens 160 of FIG. 10. It should be recognized that the schematic illustration of the optical path from the slit lamp light source to an examined eye is merely an example, and the slit lamp biomicroscope illuminating system may include an oblique mirror to redirect the light beam to the indirect ophthalmoscopy lens or examined eye. In either case, the optical device 160 being of negative or positive refractive power is positioned closely adjacent to the condensing lens 158 of the biomicroscope to achieve the desired beam enlargement for full illumination in the indirect ophthalmoscopy lens 162 as shown in FIG. 10. In this way, the maximum area of the fundus 168 of the eye is illuminated which will produce the maximum size aerial image from the indirect ophthalmoscopy lens 162.

It should be understood that the power of the lens utilized in the optical device of the invention to produce adequate divergence of the incident light beam may vary with the distance of the lens from the condensing lens of the slit lamp, wherein an increased distance from the condensing lens will require a stronger refractive powered lens. As an example where the optical device of the invention is positioned closely adjacent to the condensing lens of the biomicroscope, lens powers ranging from $-20$ diopters to $+20$ diopters may be adequate for the present state-of-the-art slit lamp biomicroscopes available from different manufacturers, and for the amounts of divergence of the incident light beam needed for the range of diameters of indirect ophthalmoscopy lenses normally used in conjunction with examinations using slit lamp biomicroscopes. The lenses having refractive power may be used in conjunction with filtering lenses if desired, by means of providing a plurality of lenses on the optical device or be utilization of a plurality of devices with the slit lamp biomicroscope.

The use of a lens which has refractive power will also provide the desired enhancement of the image produced by an indirect ophthalmoscopy lens when used to examine eyes with small pupillary apertures. As an example, when the slit of the slit lamp is fully opened, the effective light source is the circular image of the aperture of the slit lamp which is generally about one centimeter in diameter. The incident light beam on an indirect ophthalmoscopy lens will be only slightly larger than the sharply focused circular image of the aperture since the indirect ophthalmoscopy lens is held at a distance from the object plane of the biomicroscope which is equal to the short anterior focal distance of the indirect ophthalmoscopy lens, which itself is held approximately the same distance from the entrance pupil of the eye. The converging bundles of parallel light rays from the effective slit lamp light source generated at the slit lamp aperture are directed toward a relatively large circular cross-sectional area in the secondary focal plane of the indirect ophthalmoscopy lens. The bundles of parallel light rays are then refracted by the cornea and aqueous humor of the examined eye, and the cross-sectional area is formed at approximately the pupil of the examined eye. The light rays will be further refracted by the crystalline lens and vitreous humor of the eye to a focus at the fundus of the examined eye. As an example, using a large diameter indirect ophthalmoscopy lens, the circular cross-sectional area at the pupil will be approximately 4 mm in diameter with a 60 diopter lens. If the pupil of the examined eye is smaller than the 4 mm diameter, some of the light from the indirect ophthalmoscopy lens will be blocked from the fundus by the pupillary aperture. Such blockage of the illuminating light will result in a decrease of brightness and a decrease in size of the illuminated area of the fundus with a corresponding effect upon the aerial image produced by the indirect ophthalmoscopy lens. The size of the converged incident light beam from the slit lamp light source may be reduced by the optical device of the invention at the center of the entrance pupil of the examined eye so as to permit illumination of the fundus corresponding to the full extent of the fully illuminated indirect ophthalmoscopy lens through a small pupil.

The interrelated objects of producing an enlargement of the incident light beam on an indirect ophthalmoscopy lens or a reduction of size of the image of the slit lamp light source at the pupil of the examined eye are accomplished by the dissociation and repositioning of the effective slit lamp light source from its coplanar position with respect to the object plane of the biomicroscope by means of the optical device of the invention. These aspects along with the desirable aspects of providing modification of the optical characteristics of the light source be means of filters or the like provide an optical device which allows great adaptability of the slit lamp biomicroscope.

It will be evident to those skilled in the art that the invention is not limited to the details of the foregoing illustrative embodiments, and that the present invention may be embodied in other specific forms without departing from the spirit or scope thereof. Therefore, the present embodiments are to be considered as illustrative only and not restrictive as to the scope of the invention as defined in the appended claims.

I claim:

1. A lens attachment for a slit lamp biomicroscope comprising;
a microscope means and an illumination system having a housing associated therewith, wherein said illumination system housing includes an exit opening through which illuminating light is directed toward the eye of a patient to be examined with said lens attachment comprising a mounting means which is selectively positioned and supported relative to said exit opening of said illumination system housing at a predetermined position;
at least one lens associated with said mounting means to allow said at least one lens to be selectively disposed in a position between said exit opening of said illumination system and the eye of a patient in the path of the illuminating light beam generated by said illumination system without interfering with the optical pathway of said microscope means to allow selective modification of the optical characteristics of the illuminating light beam.

2. The optical device of claim 1, wherein, said at least one lens is of negative refractive power, with a dioptric value within the range of $-1.0$ to $-20.0$ diopters.

3. The optical device of claim 1, wherein, said at least one lens is of positive refractive power, with a dioptric value within the range of 1.0 to 20.0 diopters.

4. The optical device of claim 1, wherein, said at least one lens is made of homogenous transparent plastic.

5. The optical device of claim 1, wherein, said at least one lens is made of homogenous transparent glass.

6. The optical device of claim 1, wherein, said at least one lens is a filter which will filter out a predetermined portion of the spectrum of light passing therethrough.

7. The optical device of claim 6, wherein, said filter is a color filter which will filter out a portion of the visible spectrum of the light passing therethrough.

8. The optical device of claim 6, wherein, said filter is a polarizing filter acting to polarize the light passing therethrough in a specific direction.

9. The optical device of claim 1, wherein, said lens is a compound lens which comprises at least two lenses which act together to modify said illuminating light beam.

10. The optical device of claim 1, wherein, said mounting means includes means to selectively secure at least one lens therein so as to enable selective removal and replacement of said at least one lens.

11. The optical device of claim 1, wherein, said mounting means includes at least one lens holding portion which is selectively detachable from said mounting means to enable selective replacement of said at least one lens holding portion and thereby of said at least one lens.

12. The optical device of claim 1, wherein, said mounting means includes a plurality of lens holding portions, each of which include at least one lens with each being selectively positionable within the path of the illuminating light beam.

13. The optical device of claim 1, wherein, said mounting means has a semi-circular portion with a longitudinal gap therein which is dimensioned to be selectively positionable on the support structure of said illumination system of the slit lamp biomicroscope.

14. The optical device of claim 13, wherein, said semi-circular portion is dimensioned so as to have a slightly smaller diameter than the diameter of said support structure so as to enable frictional engagement of said mounting means to said support structure and to allow selective rotation thereof on said support structure.

15. The optical device of claim 1, wherein, said mounting means includes at least one lens holding portion which is hingedly engaged to said mounting means to allow said at least one lens holding portion to pivot into and out of the path of the illuminating light.

16. The optical device of claim 1, wherein, said mounting means includes means to adhere it to said slit lamp biomicroscope in a predetermined position and includes at least one lens holding portion wherein said at least one lens holding portion is selectively positionable in the path of the illuminating light.

* * * * *